(12) United States Patent
Moussy et al.

(10) Patent No.: US 8,906,357 B2
(45) Date of Patent: Dec. 9, 2014

(54) TREATMENT OF MULTIPLE SCLEROSIS WITH MASITINIB

(75) Inventors: Alain Moussy, Paris (FR); Jean-Pierre Kinet, Aix-en-Provence (FR)

(73) Assignee: AB Science, Paris (FR)

( * ) Notice: Subject to any disclaimer, the term of this patent is extended or adjusted under 35 U.S.C. 154(b) by 0 days.

(21) Appl. No.: 13/640,857

(22) PCT Filed: Apr. 20, 2011

(86) PCT No.: PCT/EP2011/056297
§ 371 (c)(1),
(2), (4) Date: Mar. 28, 2013

(87) PCT Pub. No.: WO2011/131705
PCT Pub. Date: Oct. 27, 2011

(65) Prior Publication Data
US 2013/0202555 A1    Aug. 8, 2013

Related U.S. Application Data

(60) Provisional application No. 61/325,947, filed on Apr. 20, 2010.

(51) Int. Cl.
*A61K 31/496*    (2006.01)
*A61K 45/06*    (2006.01)
*A61K 31/33*    (2006.01)

(52) U.S. Cl.
CPC .............. *A61K 31/496* (2013.01); *A61K 31/33* (2013.01); *A61K 45/06* (2013.01)
USPC ..................... 424/85.6; 424/133.1; 514/253.1

(58) Field of Classification Search
None
See application file for complete search history.

(56) References Cited

U.S. PATENT DOCUMENTS

2006/0063756 A1    3/2006    Salituro et al.
2008/0107618 A1    5/2008    Kepley

OTHER PUBLICATIONS

Vermersch Patrick et al., "Oral Masitinib . . . Multiple Sclerosis", Neurology, Lippincott Williams & Wilkins, Philadelphia, USA, vol. 72, No. 11, Mar. 1, 2009, XP00914596.
Letourneau et al., "Ultrastructural evidence . . . allergic encephalomyelitis", Journal of Neuroimmunology, vol. 145, issue 1, pp. 18-23, Dec. 2003.
Lublin et al., "Defining the . . . multiple sclerosis:", American Academy of Neurology, Neurology 46, Apr. 1996, pp. 907-911.
McDonald et al., "Recommended Diagnostic . . . Multiple Sclerosis", Ann Neurol (2001) 50:121-127.
MSFC "Multiple Sclerosis Functional Composite", National Multiple Sclerosis Society, http://www.nationalmssociety.org/ms-clinical-care-network/researchers . . . (1999).
MSQLI "Multiple Sclerosis . . . Life Inventory", National Multiple Sclerosis Society, http://www.nationalmssociety.org/ms-clinical-care-network/researchers . . . (1999).
Polman et al., "Diagnostic Criteria . . . "McDonald Criteria"", Ann Neurol 2005; 58:840-846.
Rejdak et al., "CSF Nitric oxide . . . multiple sclerosis", Neurology 2004;63:1439-1445.
Skaper et al., "Mast Cell . . . Oxide Pathway" Journal of Neurochemistry, 1996, vol. 66, No. 3, 1157-1166.
Theoharides et al., "Critical role . . . acute stress", Journal of Neuroimmunology 146 (2004) 1-12.
Theoharides et al., "Human mast cells . . . multiple sclerosis", Ann N Y Acad. Sci., PubMed, Nov. 2008; 1144: 74-82; Abstract only.
Zappulla et al., "Mast cells: . . . sclerosis therapy?", Journal of Neuroimmunology 131 (2002), 5-20.
Bebo et al., "Hypothesis: A . . . Encephalomyelitis" Journal of Neuroscience Research 45: 340-348, (1996).
Bidri et al., "Mast cells . . . nitric oxide", International Immunopharmacology 1 (2001) 1543-1558.
Hohlfeld et al., "Progress in . . . nervous system" Semin Immunopathol (2009) 31: 437-438.
Brenner et al., "Mast cells . . . and neuropeptides" J. Neurol. Sci. Apr. 1994; 122 (2) 210-3.
Brown et al., "Mechanisms underlying . . . disease course" Molecular Immunology 38 (2001) 1373-1378.
European Medicines Agency, London, Nov. 16, 2006, Doc. Ref. CPMP/EWP/561/98 Rev.1.
Cutter et al., "Development of . . . outcome measure" Brain (1999), 122, 871-882.
Dubreuil et al., "Masitinib (AB1010) . . . Targeting KIT", Plos One, vol. 4, issue 9, e7258 Sep. 2009.
FSS and EDSS, National Multiple Sclerosis Society, "Functional Systems . . . Status Scale (EDSS)", http://www.nationalmssociety.org/ms-clinical-care-network/researchers . . . (1983) pp. 1-2.
Encinas et al., "Nitric Oxide and Multiple Sclerosis" Current Neurology and Neuroscience Reports, (2005) 5:232-238.
Esposito et al., "Corticotropin-Releasing . . . Acute Stress", The Journal of Pharmacology and Experimental Therapeutics, 2002, vol. 303, No. 3, pp. 1061-1066.
Fischer et al., "Recent developments . . . multiple sclerosis", Mult. Scler. Aug. 5, 1999, (4) 251-9.
Fischer et al., "Multiple Sclerosis Functional Composite" Administration and Scoring Manual, Oct. 2001, National Multiple Sclerosis Society, pp. 1-41.
Gilfillan et al., "Integrated signaling . . . mast-cell activation" Nature Publishing Group, Mar. 2006, vol. 6, 218-230.
Kurtzke, "Rating neurologic . . . status scale", Neurology, Nov. 1983 ; 33(11) : 1444-52.

*Primary Examiner* — John Ulm
(74) *Attorney, Agent, or Firm* — Clark & Brody

(57) ABSTRACT

The present invention relates to a tyrosine kinase inhibitor or a mast cell inhibitor, and in particular masitinib or a pharmaceutically acceptable salt thereof, for the treatment of human multiple sclerosis.

24 Claims, 1 Drawing Sheet

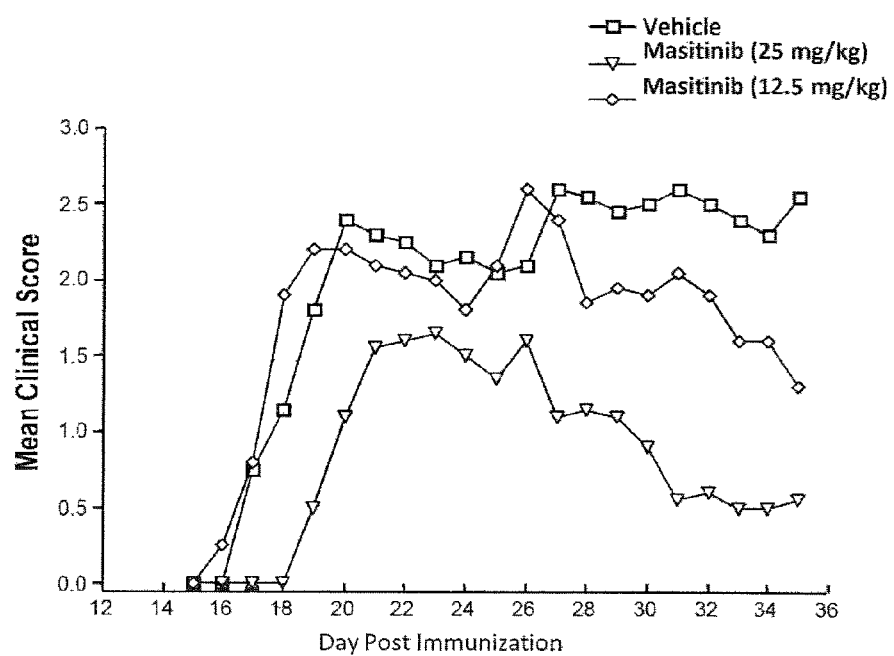

TREATMENT OF MULTIPLE SCLEROSIS WITH MASITINIB

The present invention relates to the treatment of multiple sclerosis (MS). The present invention relates to the administration of masitinib in an appropriate dosage regimen, and in particular in the treatment of MS.

BACKGROUND OF THE INVENTION

Multiple Sclerosis

Multiple Sclerosis (MS) is a common neurological disease affecting more than 1 million people worldwide (EMEA CHMP Guideline on MS, 2007). Its prevalence rate varies between races and geographical latitude, ranging from more than 100 per 100,000 in Northern and Central Europe to 50 per 100,000 in Southern Europe. MS is an inflammatory condition that damages the myelin of the Central Nervous System (CNS; the brain, spinal cord and optic nerves) and causes neurologic impairment and, frequently, severe disability. It is the commonest cause of neurological disability in young and middle-aged adults and has a major physical, psychological, social and financial impact on patients and bodies responsible for health care.

The etiology of MS remains unknown. It is generally assumed that MS is mediated by some kind of autoimmune process, an abnormal response of the body's immune system against the myelin in the CNS, possibly triggered by infection and superimposed upon a genetic predisposition. Research to date has identified the immune cells which attack the myelin, some of the factors causing them to attack, and some of the sites or receptors on the attacking cells that appear to be attracted to the myelin to begin the destructive process. However, the specific target on the myelin is yet to be identified. MS is characterized by chronic patchy inflammation of the CNS with demyelinization and gliosis (scarring). It is thought that progression of lesions in MS might have two components: an active immunological aspect and a degenerative aspect; it is unknown to what extent these are causally interrelated.

Two principal clinical courses were classified 20 years ago by the US National Multiple Sclerosis Society; relapse remitting MS and chronic progressive MS. These were further refined in 1996 by Lublin & Reingold into four clinical courses of the disease, currently recognized as: Relapsing Remitting MS (RRMS), Secondary Progressive MS (SPMS), Primary Progressive MS (PPMS) and Progressive Relapsing MS (PRMS). Each of these categories can be mild, moderate, or severe. Other very rare forms of MS also exist. More specifically, RRMS is the initial course in 80 to 85% of people diagnosed with MS and is characterized by unpredictable clearly defined relapses (flare-ups or exacerbations) of worsened neurological functioning with partial or complete recovery periods (remissions), during which no disease progression occurs. Remissions last for a period of months or years and impairments suffered during attacks may resolve or leave sequelae. Following an initial period of RRMS, many sufferers develop a secondary-progressive disease course in which the disease worsens more steadily between acute attacks, without definite periods of remission, or stable periods. Occasional relapses and minor remissions may occur. Approximately 50% of RRMS patients develop SPMS within 10 years, and after 25 to 30 years, the percentage rises to 90%. Approximately 10-15% of people diagnosed with MS have PPMS, which is characterized by slowly worsening neurologic function from the outset, with no distinct relapses or remissions.

The rate of progression may vary over time, with occasional periods of stability and temporary minor improvements. The age of onset is later than for other clinical courses. In PRMS (approximately, 5% of people diagnosed with MS), patients experience steady neurological decline from disease onset, but with clear attacks of worsening function. They may or may not experience some recovery following these relapses, but the disease continues to progress without remissions. Finally, the term clinically isolated syndrome (CIS) applies to those patients who have suffered a single clinical event but do not comply with the diagnostic criteria for definite MS.

While the four main courses of MS are currently defined according to clinical characteristics, there is increasing evidence of distinct pathological and pathogenic mechanisms between the different courses. Relapses are considered the clinical expression of acute inflammatory focal lesions whereas progression is considered to reflect the occurrence of demyelination, axonal loss and gliosis. These differences are important as they reflect differences in prognosis and because disease modifying drugs are currently effective only in the relapsing types of MS, i.e. patients either with a RRMS form or a SPMS form that are suffering relapses. Patients with relapsing MS constitute a common target for therapeutic treatments, indeed, RRMS and SPMS can be considered as different stages of the same disease while PPMS may imply different processes.

There is currently no treatment proven to slow the progression of PPMS, nor curative treatment for MS. In general, current therapeutic approaches include: symptomatic treatment, corticosteroids for acute relapses, and treatment aimed to modify the course of the disease (disease modifying drugs).

Symptomatic treatments refer to all therapies applied to improve symptoms caused by the disease: fatigue, spasticity, ataxia, weakness, bladder and bowel disturbances, sexual dysfunction, pain, tremor, paroxysmal manifestations, visual impairment, psychological problems, cognitive dysfunction and other associated conditions that can improve with non specific treatments. Disease modifying drugs are therapies aimed to decrease the relapse rate or modify relapses and to diminish the accumulation of disability in time (Table 1). While disease modifying medications may impact how quickly patients move from RRMS to SPMS and potentially the overall number of patients developing this course, long term data are not yet available. Currently approved therapies to modify the MS course target the immunological processes of the disease. Most of them are considered to act as immunomodulators but their mechanisms of action have not been completely elucidated. Immunosupressants or cytotoxic agents are also used in some patients after failure of conventional therapies. Based on the immunological nature of the disease, combination therapy targeting different parts of the immune processes may also be a possible strategy.

TABLE 1

| FDA Approved Disease Modifying Therapies for MS | | | |
|---|---|---|---|
| Active agent | Drug | FDA approval | Approved Indication |
| interferon beta 1b | Betaseron | 1993 | Treatment of relapsing forms of MS and SPMS with relapses; and after a first clinical episode with MRI features consistent with MS |

TABLE 1-continued

FDA Approved Disease Modifying Therapies for MS

| Active agent | Drug | FDA approval | Approved Indication |
|---|---|---|---|
| interferon beta 1b | Extavia | 2009 | Treatment of relapsing forms of MS and SPMS with relapses; and after a first clinical episode with MRI features consistent with MS |
| interferon beta 1a | Avonex | 1996 | Treatment of relapsing forms of MS, and for a first clinical episode if MRI features consistent with MS are also present |
| glatiramer acetate | Copaxone | 1996 | Treatment RRMS; and for a first clinical episode if MRI features consistent with MS |
| mitoxantrone | Novantrone | 2000 | Treatment of RRMS and progressive-relapsing or SPMS |
| interferon beta 1a | Rebif | 2002 | Treatment of relapsing MS |
| natalizumab | Tysabri | 2004/ 2006* | Treatment of relapsing forms of MS as a monotherapy (not used in combination with any other disease-modifying medication). |

*Voluntarily withdrawn from the market on Feb. 28, 2005; US FDA March 2006 Advisory Panel recommended for re-approval.

Despite these approved therapies, the unmet medical need in the MS field remains substantial, even for relapsing MS patients treated early and in particular for the populations of PPMS and relapse-free SPMS (rfSPMS). Several reasons can be given for this:

None of the available drugs completely stop the disease process.

MS progression can be at an advanced stage before any diagnosis is made and advanced MS is not highly responsive to treatment with any of the available drugs.

None of the drugs have been shown to be effective in rfSPMS or PPMS, subpopulations in which inflammation appears to be less prominent.

There is a suspicion that inflammation alone cannot entirely explain the progressive neurodegeneration, particularly later in the disease.

Many of the standard treatments require regular injections or infusions which, considering the chronic nature of this disease, impact negatively on the patient's adherence to treatment, quality of life and can lead to a common side effect of injection site reactions.

MS follows a highly heterogeneous disease progression, yet patient-optimized treatment, e.g. weight-adjusted dosing, is not developed in the currently available drugs.

Long-term treatment regimens using corticosteroids are associated with numerous detrimental side effects, with its benefits possibly outweighed by potential complications.

Role of c-Kit and Mast Cells in Inflammation

Mast cells (MC) are predominantly found in tissues at the interface between the host and the external environment, such as lung, connective tissue, lymphoid tissue, gut mucosa, and skin. They develop from a common circulating CD34+/c-Kit+/CD13+/FcɛRI− hematopoietic progenitor representing a single lineage, which gives rise to different phenotypes after migrating into peripheral tissues. Immature MC progenitors circulate in the bloodstream and differentiate in tissues. These differentiation and proliferation processes are influenced by cytokines, notably Stem Cell Factor (SCF), also termed Kit ligand (KL), Steel factor (SL) or Mast Cell Growth Factor (MCGF). The SCF receptor is encoded by the proto-oncogene c-Kit. It has been shown that SCF regulates the migration, maturation, proliferation, and activation of MCs in vivo—injection of recombinant SCF into rodents, primates, or humans, results in an increase in MC numbers at both the site of injection and at distant sites.

Binding of SCF to the c-Kit receptor induces c-Kit dimerization followed by its transphosphorylation, leading to the recruitment and activation of various intracytoplasmic substrates. These activated substrates induce multiple intracellular signaling pathways responsible for cell proliferation and activation. MCs are characterized by their heterogeneity, not only regarding tissue location and structure but also at functional and histochemical levels. MC activation is followed by the controlled release of a variety of mediators that are essential for the defense of the organism against invading pathogens. By contrast, in the case of hyperactivation of MCs, uncontrolled hypersecretion of these mediators is deleterious for the body. MCs produce a large variety of mediators categorized here into three groups:

Preformed granule-associated mediators (histamines, proteoglycans, and neutral proteases);

Lipid-derived mediators (prostaglandins, thromboxanes and leucotrienes);

Various cytokines (including the interleukins: IL-1, IL-2, IL-3, IL-4, IL-5, IL-6, IL-8 and tumor necrosis factor alpha TNF-α, GM-CSF, MIP-1α, MIP-1β and IFN-γ).

Human MCs constitutively express a number of receptors for different biological molecules. Among these receptors, whose ligation induces the activation of MCs, the best known is the high affinity receptor for IgE (FcER1). Binding of IgE-multivalent antigen complexes to FcER1 leads to receptor aggregation and internalization, signaling, and degranulation. This can be accompanied by the transcription of cytokine genes, thus, perpetuating the inflammatory response. Moreover, triggering of MCs leads to the secretion of diverse pre-formed and/or de novo synthesized mediators, such as vasoactive amines (histamine, serotonin), sulfated proteoglycans, lipid mediators (prostaglandin D2, leucotrienes), growth factors, proteases, cytokines and chemokines as described previously. These mediators can, alone or in synergy with macrophage-derived and T cell-derived cytokines, generate a complex inflammatory response and induce the recruitment and activation of inflammatory cells to the site of degranulation.

AIMS OF THE INVENTION

The invention aims to solve the technical problem of providing an active ingredient for the treatment of MS, and in particular either one or more of Relapsing Remitting MS (RRMS), Secondary Progressive MS (SPMS), Primary Progressive MS (PPMS) and Progressive Relapsing MS (PRMS).

The invention also relates to the treatment of such a disease in a human patient.

The invention aims to provide an efficient treatment for such a disease at an appropriate dose, route of administration and daily intake.

SUMMARY OF THE INVENTION

The invention relates to a tyrosine kinase inhibitor or a MC inhibitor, and in particular masitinib or a pharmaceutically acceptable salt thereof, for the treatment of MS, and in particular according to the 'McDonald criteria' or according to classifications of the US National Multiple Sclerosis Society (Relapsing Remitting MS, Secondary Progressive MS with and without relapses, Primary Progressive MS and Progressive Relapsing MS), in human patients, wherein masitinib is to be administered daily at a starting dose of 3.0 to 6.0±1.5, and preferably 4.5 to 6.0±1.5, mg/kg/day and wherein said patients are between 1.0 to 6.5 on the expanded disability status scale (EDSS).

The invention also relates to a method of treatment of MS, and in particular according to the 'McDonald criteria' or according to classifications of the US National Multiple Sclerosis Society (Relapsing Remitting MS, Secondary Progressive MS with and without relapses, Primary Progressive MS and Progressive Relapsing MS), in human patients, wherein a tyrosine kinase inhibitor or a MC inhibitor, and in particular masitinib or a pharmaceutically acceptable salt thereof, is to be administered daily at a starting dose of 3.0 to 6.0±1.5, and preferably 4.5 to 6.0±1.5, mg/kg/day, and wherein said patients are between 1.0 to 6.5 on the expanded disability status scale (EDSS).

BRIEF DESCRIPTION OF THE DRAWING

The sole FIGURE shows the effect of masitinib on the clinical score in a mouse EAE model of MS.

DESCRIPTION OF THE INVENTION

Mast Cells in Multiple Sclerosis

Several findings support the hypothesis that mast cells (MC) and other elements of the allergic immune response are involved in MS and experimental allergic encephalomyelitis (EAE), an animal model of human demyelinating diseases, including MS (Brandl & Lassman, 2009; Brown et al., 2001; Theoharides et al., 2008; Theoharides et al. 2004). Increased permeability of the Blood-Brain Barrier (BBB) is an early event in the development of clinical or pathologic findings in EAE and MS and perivascular brain MCs secreting vasoactive and pro-inflammatory molecules contribute to the pathological cascade (Esposito et al. 2002; Letourneau et al. 2003). Sites of inflammatory demyelination contain cellular infiltrates with MC accumulation in the brain and spinal cord (Bebo et al. 1996), and the percentage of degranulated MCs in the central nervous system correlates with the clinical onset of disease symptoms in acute EAE (Brenner et al. 1994). Furthermore, MC-deficient mice exhibit significantly reduced disease severity compared to wild-type littermates in a murine model of MS and drugs that block MC function can improve clinical symptoms in this model.

Masitinib is a Potent Mast Cell Inhibitor

Masitinib is a small molecule selectively inhibiting specific tyrosine kinases such as c-kit, PDGFR, Lyn and to a lesser extent the fibroblast growth factor receptor 3 (FGFR3), without inhibiting, at therapeutic doses, kinases associated with known toxicities (i.e. those tyrosine kinases or tyrosine kinase receptors attributed to possible tyrosine kinase inhibitor cardiac toxicity, including ABL, KDR and Src) (Dubreuil et al, 2009). The chemical name for masitinib is 4-(4-methylpiperazin-1-ylmethyl)-N-[4-methyl-3-(4-pyridin-3ylthiazol-2-ylamino) phenyl]benzamide—CAS number 790299-79-5, and the structure is shown below.

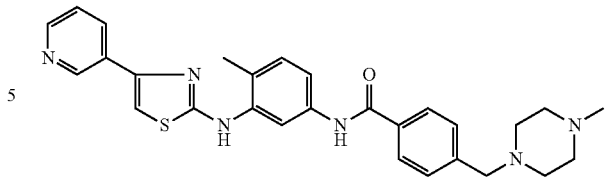

Masitinib was first described in U.S. Pat. No. 7,423,055 and EP1525200B1. A detailed procedure for the synthesis of masitinib mesilate is given in WO2008/098949.

Masitinib's strong inhibitory effect on wild-type and juxtamembrane-mutated c-Kit receptors, results in cell cycle arrest and apoptosis of cell lines dependent on c-Kit signaling (Dubreuil et al., 2009). Stem cell factor, the ligand of the c-Kit receptor, is a critical growth factor for MCs, essential to their survival, proliferation, differentiation, adhesion and degranulation processes. Thus, masitinib is an effective antimastocyte, exerting a direct antiproliferative and pro-apoptotic action on MCs through its inhibition of c-Kit signaling. In addition to its antiproliferative properties, masitinib can also regulate the activation of MCs through its targeting of Lyn and Fyn, key components of the transduction pathway leading to IgE induced degranulation (Gilfillan & Tkaczyk, 2006). This can be observed in the inhibition of FcER1-mediated degranulation of human cord blood MCs (Dubreuil et al., 2009).

Treatment of Multiple Sclerosis with Masitinib

MCs play a prominent role in all the inflammatory processes and actively participate in the pathogenesis of MS, in part because they release large amounts of various mediators that sustain the inflammatory network. Thus, molecules able to inhibit the survival and/or activation of MCs may be able to control the symptoms and progression of MS or any related disease. In connection with the present invention, we consider that masitinib, through its inhibition of MC proliferation and activation, is fulfilling this role in the treatment of MS via, but not limited to, inflammatory-mediated and nitric oxide-mediated neuronal damage mechanisms. Through its inhibition of both c-Kit and Lyn kinase activity, masitinib acts on MCs, affecting in vitro their migration and activation and inducing their death. This could limit the role of MCs in the early increased permeability of the BBB, reduce their number at the sites of inflammatory demyelination and reduce the inflammation linked to MCs degranulation. The mechanism of action of masitinib is original and there is currently no other drug directed against these targets in MS in phase 2 or 3 clinical trials.

The role of inflammation in the development of brain injury in MS is well-established (Brandi & Lassman, 2009). A highly significant correlation exists between inflammation and acute axonal injury, with neurodegeneration being driven by inflammation during the progressive phase of the disease. In PPMS, inflammation is thought to be trapped behind the BBB, and damage is in part provoked by soluble inflammatory mediators. It has been reported that in the context of the experimental allergic encephalomyelitis (EAE) model, MCs are necessary for the full manifestation of MOG-induced EAE disease (Brown et al., 2001). Recently, Theoharides et al. (2008) reviewed the role of brain MCs in MS. Perivascular MCs secrete pro-inflammatory and vasoactive molecules that can disrupt the BBB, a finding that precedes clinical or pathological signs of MS. Brain MCs are activated in MS by neural factors, including substance P, myelin basic protein, and corticotropin-releasing hormone, caused by acute stress, which induce release of several inflammatory mediators. MCs can stimulate activated T-cells with which they come into contact at the BBB. MCs can thus be considered a promising target in the treatment of MS (Zappulla et al. 2002).

In connection with the present invention, it would seem, without wishing to be bound by the theory, that surprisingly masitinib could also provide protection against possible mast cell-induced nitric oxide-mediated neuronal damage mechanisms. Although a topic of debate, there is growing evidence that the different courses of MS, i.e. relapsing as opposed to relapse-free, are due to distinct pathophysiologic processes. That is, RRMS and SPMS are probably different stages of the same disease while PPMS may imply different processes. This distinction in MS types appears to be reflected by the unsuccessful treatment of PPMS with powerful disease modifying drugs, which in turn may relate to the dominant cause of progression of disability in PPMS being more strongly related to nerve cell death, in addition to inflammation-induced neuronal damage (swelling) commonly attributed to relapsing forms of MS. Abundant evidence indicates an important role for nitric oxide (NO) in the pathogenesis of MS and to its contribution to the various facets of the disorder (Encinas et al., 2005), especially for those patients in progression (Rejdak et al., 2004). The action of NO may have both positive and negative effects on the development of the disease, with one deleterious role being that NO and its progenitors are potentially toxic molecules and have been related to NO-mediated damage to oligodendrocytes and neurons. In vitro experiments by Skaper et al., 1996, showed that MC activation lead to neuronal damage by astrocyte/NO-dependent and -independent pathways. Specifically, the cognate MC line RBL-2H3, when subjected to an antigenic stimulus, released TNF-α which, together with exogenous interleukin-1β (or interferon-γ), induced astroglia to produce neurotoxic quantities of NO. It has also been reported that MCs can be a source of NO derivatives, which they synthesize spontaneously or following activation, depending on their subtype (Bidri et al., 2001). This evidence supports the notion that MCs, which can be found in close vicinity to neurons, could influence the survival and functions of NO-sensitive cells and through this mechanism participate in the pathophysiology of chronic neurodegenerative diseases of the nervous system. It further suggests that down-modulation of MC activation in such conditions could be of therapeutic benefit.

The ability and effect of masitinib in the inhibition of MC function in MS was explored using the EAE murine model. The myelin oligodendrocyte glycoprotein (MOG)-induced disease in C57BL/6 mice is considered to be a model for all progressive foinis of MS. C57BL/6 mice were immunized with 300 ng MOG35-55 peptide (an immunological target in the human disease) on days 0 (in complete Freund's adjuvant) and 7 (in incomplete Freund's adjuvant) and 250 ng pertussis was administered intravenously on days 0 and 2. Mice were scored daily by visual assessment of symptoms on a scale of 0-5 where 1 denotes a flaccid tail, 2 denotes hind limb weakness, 3 denotes hind limb paralysis, 4 denotes an inability to right from supine and 5 indicates death. Statistical analyzes of significance between mean clinical scores were performed using Bonferroni's Multiple Comparison Test-One way ANOVA or paired t tests. Statistical analyses were performed for the daily intervals between days 26-35. Five mice per experimental group were administrated the following treatment every day from the first day of immunization (day 0):

Vehicle (PBS)
Masitinib 25 mg/kg, 2 times per day, intraperitoneal injection
Masitinib 12.5 mg/kg, 2 times per day, intraperitoneal injection The sole FIGURE shows the effect of masitinib on the clinical score in the mouse EAE model of MS.

Between days 26-35, treatment with masitinib at both doses resulted in significant differences in mean clinical score (the sole figure), which also reflects the apparent delayed protective effects of masitinib treatment observed using both doses. A dose response between 25 mg/kg and 12.5 mg/kg is also observed.

| Vehicle versus masitinib 25 mg/kg | $p < 0.001$ |
| Vehicle versus masitinib 12.5 mg/kg | $p < 0.001$ |
| Masitinib 25 mg/kg versus masitinib 12.5 mg/kg | $p < 0.001$ |

In summary, treatment of mice with masitinib led to a significant reduction in disease relative to mice treated with vehicle alone, as assessed by the mean clinical score. There appears to be a masitinib dose-dependent effect, and also a delayed response to masitinib at both doses.

The in vitro evidence that masitinib's ability to target MCs is a viable therapeutic strategy in MS is further strengthened by our proof-of-concept in vivo and phase 2 trials investigating the effect of masitinib at different dosage regimens in patients with MS. These clinical trials indicate that masitinib can be of potential therapeutic benefit across the spectrum of MS subpopulations with RRMS, SPMS and PPMS patients showing positive response in some relevant functions of MS (see Examples #1 and #2 for detailed description). Unexpectedly, masitinib treatment showed promising therapeutic effect on rfSPMS patients and to an even greater extent on PPMS patients, for which there are currently no therapeutic options. Thus, masitinib's anitmastocyte properties may be particularly well adapted to the treatment of PPMS; a reduction of MC activity via the inhibitory action of masitinib on c-Kit, Lyn and Fyn tyrosine kinase activity, impacting both inflammatory-mediated and NO-mediated damage mechanisms. Surprisingly, it would seem, without wishing to be bound by the theory, it is through this multifaceted action, and possibly unique pathophysiology of PPMS, that masitinib may potentially elicit a response in both relapsing and relapse-free forms of MS, which has not been demonstrated with any currently available treatments.

The present invention relates in particular to the use of tyrosine kinase inhibitor or a MC inhibitor, and in particular masitinib or a pharmaceutically acceptable salt thereof for the preparation of a medicament for the treatment of multiple sclerosis (MS) according to the 'McDonald criteria' or according to classifications of the US National Multiple Sclerosis Society (Relapsing Remitting MS, Secondary Progressive MS with and without relapses, Primary Progressive MS and Progressive Relapsing MS), in human patients, wherein masitinib is to be administered daily at a starting dose of 3.0 to 6.0±1.5, and preferably 4.5 to 6.0±1.5, mg/kg/day, (optionally combined with at least one disease modifying drug at an appropriate dose), and wherein said patients are between 1.0 to 6.5 on the expanded disability status scale (EDSS). The preferred embodiment for patients with relapse-free Secondary Progressive Multiple Sclerosis or Primary Progressive Multiple Sclerosis is a starting daily dose of 4.5 to 6.0 mg/kg/day.

The invention also relates in particular to a method of treatment of MS according to the 'McDonald criteria' or according to classifications of the US National Multiple Sclerosis Society, in human patients, wherein tyrosine kinase inhibitor or a MC inhibitor, and in particular masitinib or a pharmaceutically acceptable salt thereof, is to be administered daily at a starting dose of 3.0 to 6.0±1.5, and preferably 4.5 to 6.0±1.5, mg/kg/day, (optionally combined with at least one disease modifying drug at an appropriate dose), and wherein said patients are between 1.0 to 6.5 on the expanded disability status scale (EDSS).

In one embodiment said tyrosine kinase inhibitor or MC inhibitor, and in particular masitinib or a pharmaceutically acceptable salt thereof, is administered for the treatment of relapse-free forms of MS, and in particular for the treatment of relapse-free Secondary Progressive MS (rfSPMS) or Primary Progressive MS (PPMS).

In another embodiment said tyrosine kinase inhibitor or MC inhibitor, and in particular masitinib or a pharmaceutically acceptable salt thereof, is administered for the treatment of relapsing Secondary Progressive MS (rSPMS) or Relapsing Remitting MS (RRMS).

Advantageously, in the use or the method above, said patients have a score of between 1.0 to 6.5 on the expanded disability status scale (EDSS). Patients according to the invention are those afflicted with MS of mild severity (i.e. minimal signs on at least one functional system but no disability) to those with severe disability but ambulatory with mobility aid (i.e. constant bilateral support required to walk 20 meters without resting); more specifically with EDSS scores of between 1.0 to 6.5, or 2.0 to 6.5 (mild disability to severe disability but ambulatory with mobility aid), or even 3.0 to 6.5 (moderate disability to severe disability but ambulatory with mobility aid).

In one preferred embodiment, masitinib is masitinib mesilate. Regarding best dosage regimen, said tyrosine kinase inhibitor or MC inhibitor, and in particular masitinib or a pharmaceutically acceptable salt thereof, is to be administered at a starting daily dose of 3.0 to 6.0 mg/kg/day; nonetheless said tyrosine kinase inhibitor or MC inhibitor, and in particular masitinib or a pharmaceutically acceptable salt thereof can be dose escalated by increments of 1.5 mg/kg/day to reach a maximum of 9.0 mg/kg/day in low responder patients.

Indeed, depending on age, individual condition, mode of administration, and the clinical setting, effective doses of said tyrosine kinase inhibitor or MC inhibitor, and in particular masitinib or a pharmaceutically acceptable salt thereof, in human patients with MS are 3.0 to 6.0 mg/kg/day per os, preferably in two daily intakes. For adult human patients with PPMS or rISPMS, a starting dose of said tyrosine kinase inhibitor or MC inhibitor, and in particular masitinib or a pharmaceutically acceptable salt thereof of, 4.5 to 6.0 mg/kg/day has been found to be the preferred embodiment according to the invention. For patients with an inadequate response after an assessment of response to therapy and in the absence of limiting toxicities, dose escalation of said tyrosine kinase inhibitor or MC inhibitor, and in particular masitinib or a pharmaceutically acceptable salt thereof to a maximum of 9.0 mg/kg/day can be safely considered and patients may be treated as long as they benefit from treatment and in the absence of limiting toxicities.

If dose escalation is undertaken, it is suggested that the starting dose of 3.0 to 6.0±1.5, and preferably 4.5 to 6.0±1.5, mg/kg/day be incremented by 1 to 2 mg/kg/day up to a maximum dose of 9.0 mg/kg/day, over a period which depends upon clinical observations. For example, a single dose escalation of said tyrosine kinase inhibitor or MC inhibitor and in particular masitinib or a pharmaceutically acceptable salt thereof, and preferably masitinib mesilate may take from 1 to 2 months. It is also contemplated herein that to fully obtain the therapeutic benefits of a patient-optimized dose of said tyrosine kinase inhibitor or MC inhibitor, and in particular masitinib or a pharmaceutically acceptable salt thereof, dose increments smaller than 1 to 2 mg/kg/day could be implemented. Dose reduction is to be considered to reduce toxicity in appropriate cases.

Dose adjustment can be considered a dynamic process, with a patient undergoing multiple increases and/or decreases to optimize the balance between response and toxicity throughout treatment, both of which are likely to vary over time and duration of drug exposure.

Any dose indicated herein refers to the amount of active ingredient as such, not to its salt form.

Pharmaceutically acceptable salts are pharmaceutically acceptable acid addition salts, like for example with inorganic acids, such as hydrochloric acid, sulfuric acid or a phosphoric acid, or with suitable organic carboxylic or sulfonic acids, for example aliphatic mono- or di-carboxylic acids, such as trifluoroacetic acid, acetic acid, propionic acid, glycolic acid, succinic acid, maleic acid, fumaric acid, hydroxymaleic acid, malic acid, tartaric acid, citric acid or oxalic acid, or amino acids such as arginine or lysine, aromatic carboxylic acids, such as benzoic acid, 2-phenoxy-benzoic acid, 2-acetoxybenzoic acid, salicylic acid, 4-aminosalicylic acid, aromatic-aliphatic carboxylic acids, such as mandelic acid or cinnamic acid, heteroaromatic carboxylic acids, such as nicotinic acid or isonicotinic acid, aliphatic sulfonic acids, such as methane-, ethane- or 2-hydroxyethane-sulfonic, in particular methanesulfonic acid (or mesilate), or aromatic sulfonic acids, for example benzene-, p-toluene- or naphthalene-2-sulfonic acid.

In a preferred embodiment of the above-depicted treatment, the active ingredient masitinib is administered in the form of masitinib mesilate; which is the orally bioavailable mesylate salt of masitinib—CAS 1048007-93-7 (MsOH); C28H30N6OS.CH3SO3H; MW 594.76:

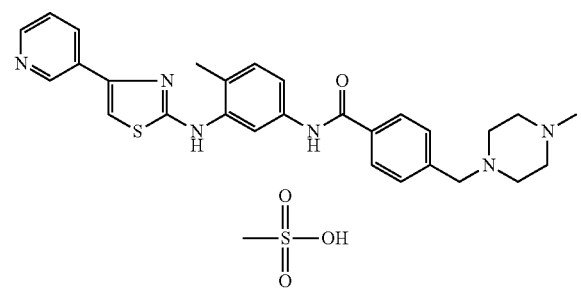

Given that the masitinib dose in mg/kg/day used in the described dose regimens refers to the amount of active ingredient masitinib, compositional variations of a pharmaceutically acceptable salt of masitinib mesilate will not change the said dose regimens.

Masitinib may be administered via different routes of administration but oral administration is preferred. Thus, in still another preferred embodiment, in the use or the method above, masitinib or salts thereof, is administered orally; preferably twice a day for long term period such as over more than 6 months, preferably more than 12 months. Masitinib can be administered in the form of 100 and 200 mg tablets.

In the present invention as defined above, the optional disease modifying drug, dosed ideally in accordance to the manufacture's recommendations, could for example be, and without particular limitation, either: an interferon beta-1a (e.g. Avonex, CinnoVex, ReciGen and Rebif); an interferon beta-1b (e.g. Betaseron or Betaferon); a non-interferon, non-steroidal immunomodulator such as glatiramer acetate (e.g. Copaxone); an immunosuppressant such as mitoxantrone; or a humanized monoclonal antibody such as natalizumab (Tysabri). In this regard, masitinib and at least one disease modifying drug are to be administered separately, simultaneously or sequentially in time.

Such medicament can take the form of a pharmaceutical composition adapted for oral administration, which can be formulated using pharmaceutically acceptable carriers well known in the art in suitable dosages. Such carriers enable the pharmaceutical compositions to be formulated as tablets, pills, dragees, capsules, liquids, gels, syrups, slurries, suspensions, and the like, for ingestion by the patient. In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of Remington's Pharmaceutical Sciences (Maack Publishing Co., Easton, Pa.).

The invention also relates to a pharmaceutical composition comprising a tyrosine kinase inhibitor or a mast cell inhibitor, and in particular masitinib or a pharmaceutically acceptable salt thereof, and preferably masitinib mesilate, optionally in combination with another pharmaceutically active ingredient, and in combination with one or more pharmaceutically acceptable excipient.

The present invention is illustrated by means of the following examples.

EXAMPLE 1

Clinical Evaluation in Patients with PPMS or Relapse-Free SPMS

A multicenter, double-blind, randomized, placebo-controlled, parallel-group, phase 2 proof-of-concept clinical trial, designed to evaluate the efficacy and safety of oral masitinib administered at 3 or 6 mg/kg/day for 12 months in patients with PPMS or rfSPMS.

Methods
Study Design and Treatment

Patients were randomized to receive orally administered masitinib at an initial dose of 3 or 6 mg/kg/day b.i.d, with two dose increases of 1.5 mg/kg/day permitted in the event of lack of activity and manageable toxicity. Masitinib and placebo were supplied as 100 or 200 mg tablets. The initial study had three arms but this was amended to close the 3 mg/kg/day bid arm after approximately 1 year. Initially, 35 patients were planned but this was later amended to at least 20 patients who had completed at least 12 months of treatment and had undergone a 12-month magnetic resonance image (MRI) assessment.

MS evaluations were performed at screening, at week 0 (baseline), at month 1, 2, 3, 6, 9, 12, 18 and 24 or at the withdrawal visit. The main efficacy endpoints included the expanded disability status scale (EDSS) score (Kurtzke et al. 1983), the multiple sclerosis functional composite (MSFC) (Cutter et al. 1999) and MS-related imaging parameters. Masitinib tolerance was assessed by clinical and biological safety parameters.

Patients

Patients of either gender, aged 18 to 60, suffering from PPMS or rfSPMS as diagnosed by the 'McDonald criteria' (McDonald et al., 2001; Polman et al., 2005) and having an Expanded Disability Status Scale (EDSS) score between 2 to 6.5 with a progression ≥1 within 2 years prior to inclusion, were eligible for this study. Patients having SPMS with relapse in the 2 years before inclusion were excluded. No oral or parenteral concomitant corticosteroids were permitted for the duration of study, except in case of protocol-defined demyelinating event (methylprednisolone at 1 g/day for 3 days). No immunomodulating, immunosuppressing, chemotherapy and paracetamol concomitant administration were permitted for the duration of the study. Concomitant analgesic without anti-inflammatory action and oral narcotic analgesic were not allowed on the day of a study visit until all efficacy evaluations were completed. Concomitant physical therapy was allowed in patients already receiving such therapy at study entry. To manage rash, a mandatory concomitant treatment (cetirizine, 10 mg/day for 30 days) was combined with masitinib.

Efficacy and Safety Assessment

Neurological functions were assessed by evolution of the EDSS score (Kurtzke et al. 1983), and the MSFC (Cutter et al. 1999). The latter is a multidimensional, MS-specific outcome measure, comprising of a timed 25-foot walk (T25FW) test measuring leg function and ambulation, a 9-hole peg test (9-HPT) measuring arm and hand function and a Paced Auditory Serial Addition Test 3 seconds (PASAT-3") measuring cognitive function. The MSFC was calculated as described in the National Multiple Sclerosis Society MSFC administration and scoring manual by averaging the z-scores from each components of the MSFC. Z-scores are calculated as the number of standard deviation units a patient's score is below or above the average score at baseline (Fischer et al. 1999b).

A multidimensional health related MS Quality Of Life (MSQLI) (Fischer et al. 1999a) measure was assessed ex-post as a secondary endpoint. Subscales were mental health inventory (MHI), health status questionnaire (SF-36), MOS modified social support survey (MSSS), modified fatigue impact scale (MFIS), MOS pain effect scale (PES), perceived deficit questionnaire (PDQ), visual impairment scale (VIS), bowel control scale (BoCS), sexual satisfaction scale (SSS), bladder control scale (BCS).

Serial MRI were performed locally using a uniform imaging protocol (MRI scanner field strength: 1.5 T) for neurological imaging. MRI reading was performed centrally (Theralys, Lyon, France). Assessed parameters included the count of lesions (T2 lesions on dual echo images, flair lesions, T1 hypointense lesions, gadolinium-enhancing (Gd+) lesions), the volume of T2 lesion, and measure of atrophy (third ventricle's width, brain parenchymal fraction, and cross sectional upper cervical cross area at the C2 level).

Adverse events (AE) were described by duration, intensity, relation to masitinib and course of action. Intensities were graded either mild (signs and symptoms are present without functional repercussions), moderate (there are functional repercussions without putting the patient's health at risk), or severe (functional alterations or incapacity or definite risk for the patient health). Hematology, blood biochemistry and urinalysis were performed at screening, at week 0, at month 1, 2, 3, 6, 9, 12, 18 and 24, or at withdrawal visit.

Results
Baseline Characteristics

Recruitment was stopped after 35 patients (27 masitinib, 8 placebo) had been randomized and 22 patients had completed the 12 months of treatment (17 masitinib, 5 placebo), six patients had 18 months of treatment (5 masitinib, 1 placebo), and four patients 21 months of treatment (4 masitinib, 0 placebo). Twelve patients started treatment on 3 mg/kg/day before being switched to 6 mg/kg/day. The modified intent-to-treat (mITT) population on which efficacy analyses were performed included 30 patients (24 masitinib, 9 with PPMS and 15 with rfSPMS; and 6 placebo, 3 each with PPMS and rfSPMS). The reason for five patients not being applicable for the mITT population were: lack of efficacy measurement after baseline (two patients; one each for placebo and masitinib) or lack of PASAT-3" assessment in the first 3 months (three patients, one receiving placebo and two receiving masitinib).

The patient demographic characteristics of patients in the intent-to-treat population were globally similar between the placebo and masitinib groups in terms of age, gender and weight. Likewise, demographic characteristics of patients were globally similar between the PPMS and rfSPMS populations. Disease characteristics were similar between the PPMS and rfSPMS populations, except for duration of disease which was longer in the rfSPMS population (12.3 years) as compared to the PPMS population (2.3 years) and was to be expected. At baseline, mean MSFC z-score was higher in the placebo group, indicating better patient function in the placebo group compared to the masitinib group. This was explained because patients in the placebo group had better mean T25FW z-score (indicating better leg/ambulation function) and better mean PASAT-3" z-score (indicating better cognitive function), despite slightly worst mean 9-HPT z-score (indicating worse arm/hand function) as compared to patients in the masitinib group. Mean MSFC z-score was also higher in the PPMS population, indicating better patient function in the PPMS population compared to the rfSPMS population. This was mainly explained because patients in the PPMS population had better T25FW compared to the rfSPMS population (12 versus 29 seconds, respectively). EDSS was overall similar between the placebo and the masitinib groups, and slightly higher in the PPMS population compared to the rfSPMS population (5.1 vs. 4.7, respectively).

TABLE 2

Summary of baseline characteristics.

|  | All n = 35 | Masitinib n = 27 | Placebo n = 8 |
|---|---|---|---|
| Median age (yrs) | 48 ± 8 | 49 ± 9 | 47 ± 7 |
| Male (%) | 17 (49) | 13 (48) | 4 (50) |
| Duration of disease (yrs) | 9.4 ± 7.4 | 9.5 ± 7.3 | 8.8 ± 8.4 |
| MSFC z-score | 0.0 ± 0.7 | −0.1 ± 0.7 | 0.3 ± 0.8 |
| T25FW z-score(s) | 22 ± 24 | 23 ± 27 | 17 ± 14 |
| 9-HPT z-score (s) | 30 ± 9 | 30 ± 9 | 31 ± 12 |
| PASAT-3" z-score | 31 ± 15 | 30 ± 15 | 36 ± 15 |
| EDSS score | 4.9 ± 1.2 | 4.9 ± 1.2 | 5.0 ± 1.1 |

Efficacy Analyses

Overall, EDSS scores remained stable over 18 months in the masitinib and placebo groups, with a mean change of <0.5 in EDSS. When analyzed by clinical course, EDSS score was stable in the PPMS population in both treatment groups. In the rfSPMS population, EDSS score remained stable in the masitinib group but increased in the placebo group (+1 point).

A change in MSFC was observed in the masitinib group as early as month 3 with a mean increase from baseline of 78%, compared to a mean decrease of 64% in the placebo group. This improvement for patients receiving masitinib was maintained throughout the study until month 18 (+96%). MSFC z-score was improved in both PPMS and rfSPMS patients. Effect of masitinib was observed as early as month 3 (+108% and +60% in the PPMS and rfSPMS populations, respectively), and was also maintained throughout the study until month 18 (+134% and +73% in the PPMS and rfSPMS populations, respectively). The increase from baseline in MSFC was mainly driven by T25FW and 9-HPT. Mean T25FW raw scores increased throughout the study; however, the increase was much milder in the masitinib group compared to the deterioration in the placebo group (+1.6 vs.+4.2 seconds at month 18, respectively). Mean 9-HPT raw scores decreased in the masitinib group whereas the score increased in the placebo group (−1.6 vs.+1.5 seconds at month 18, respectively). Mean PASAT-3" raw scores increased throughout the study in both treatment groups (+6.0 vs.+9.0 at month 18 in the masitinib group and placebo group, respectively).

TABLE 3

Summary of MSFC and EDSS efficacy data

|  |  |  | M3 | M6 | M9 | M12 | M18 |
|---|---|---|---|---|---|---|---|
| MSFC | All (n = 30) | Masitinib (n = 24) | 78 ± 284 | 156 ± 274 | 70 ± 267 | 103 ± 189 | 96 ± 191 |
|  |  | Placebo (n = 6) | −64 ± 188 | −58 ± 200 | −49 ± 193 | −60 ± 190 | −61 ± 190 |
|  | PPMS (n = 12) | Masitinib (n = 9) | 108 ± 435 | 202 ± 353 | 56 ± 410 | 134 ± 268 | 134 ± 268 |
|  |  | Placebo (n = 3) | −14 ± 40 | −20 ± 92 | 8 ± 21 | −11 ± 47 | −11 ± 47 |
|  | rfSPMS (n = 18) | Masitinib (n = 15) | 60 ± 152 | 129 ± 223 | 78 ± 146 | 84 ± 130 | 73 ± 131 |
|  |  | Placebo (n = 3) | −113 ± 281 | −96 ± 296 | −106 ± 287 | −109 ± 284 | −110 ± 284 |
| EDSS | All (n = 30) | Masitinib (n = 24) | −0.1 ± 0.3 | −0.1 ± 0.4 | −0.0 ± 0.4 | 0.0 ± 0.5 | 0.0 ± 0.5 |
|  |  | Placebo (n = 6) | 0.1 ± 0.4 | 0.0 ± 0.8 | 0.1 ± 0.8 | 0.3 ± 1.0 | 0.3 ± 1.0 |
|  | PPMS (n = 12) | Masitinib (n = 9) | −0.1 ± 0.2 | −0.2 ± 0.5 | −0.1 ± 0.4 | 0.1 ± 0.4 | 0.1 ± 0.4 |
|  |  | Placebo (n = 3) | 0.0 ± 0.4 | −0.3 ± 0.8 | −0.2 ± 0.8 | −0.2 ± 0.8 | −0.2 ± 0.8 |
|  | rfSPMS (n = 18) | Masitinib (n = 15) | −0.0 ± 0.3 | −0.0 ± 0.3 | −0.0 ± 0.3 | 0.0 ± 0.5 | 0.0 ± 0.5 |
|  |  | Placebo (n = 3) | 0.3 ± 0.6 | 0.5 ± 0.5 | 0.7 ± 0.6 | 1.0 ± 1.0 | 1.0 ± 1.0 |

Mean percentage change from baseline Last Observation Carried Forward (LOCF) data analysis.

Regarding the MS-related imaging parameters, the brain volume remained stable throughout the study in the placebo group but two patients experienced a brain volume increase in the masitinib group. No conclusion could be drawn from analyses of lesions (Gadolinium enhancing, T1 hypointense and T2 hyperintense lesions).

Efficacy results were complemented by MSQLI results evaluating quality of life over the course of treatment. Masitinib improved some MSQLI subscales, including: SF-36, Modified Fatigue Impact Scale, MOS Pain Effect scale, Perceive Deficit Questionnaire, Mental Health Inventory and Modified Social Support Survey. In contrast, patients in the placebo group either worsened or were stable.

TABLE 4

Mean percentage change from baseline for MSQLI (ex-post)

| MSQLI Subscales | Masitinib | Placebo |
| --- | --- | --- |
| MHI | 15.2 ± 25.99 (n = 9) | −11.4 ± 9.9 (n = 3) |
| SF-36 | 12.7 ± 24.3 (n = 5) | −14.1 (n = 1) |
| MSSS | 6.2 ± 9.4 (n = 7) | −2.9 ± 5.0 (n = 3) |
| MFIS | −3.0 ± 14.9 (n = 8) | 28.7 ± 34.3 (n = 3) |
| PES | −3.9 ± 12.2 (n = 7) | 22.9 ± 35.9 (n = 3) |
| PDQ | 1.1 ± 11.7 (n = 6) | 37.4 ± 60.0 (n = 3) |
| VIS | 0 ± 0 (n = 4) | 0 (n = 1) |
| BoCS | −3.1 ± 8.8 (n = 7) | 0 ± 0 (n = 3) |
| SSS | −6.9 ± 29.0 (n = 4) | 0 ± 0 (n = 2) |
| BLCS | 21.5 ± 72.4 (n = 8) | 3.9 ± 5.4 (n = 2) |

Safety Analyses

AEs (adverse events) were reported in 85% of patients treated with masitinib versus 75% of patients treated with placebo. A total of 119 AEs were reported by investigators, 100 in the masitinib group and 19 in the placebo group. No death was reported during this study. Nine patients (33%) in the masitinib group and two patients (25%) in the placebo group reported a serious, non-fatal AE. Seven patients (26%) experienced an AE leading to masitinib discontinuation (versus no patients in the placebo group). Seven patients treated with masitinib (26%) reported a severe AE that was suspected to be related to therapy (versus none receiving placebo). Patients treated with masitinib most frequently reported AEs (Table 5) were: asthenia (41% of patients), nausea (26%), diarrhea, rash, urinary tract infection and weight decrease (11% each), their intensity were mild or moderate. Most frequently reported AE (≥2 patients) reported by patients receiving placebo (Table 5) was asthenia (25%).

TABLE 5

Adverse Events most commonly reported (>10% in the masitinib group, ≥2 in the placebo group).

| Preferred term | Masitinib (n = 27) | Placebo (n = 8) |
| --- | --- | --- |
| Asthenia | 11 (41%) | 2 (25%) |
| Nausea | 7 (26%) | |
| Diarrhea | 3 (11%) | |
| Rash | 3 (11%) | |
| Urinary Tract Infection | 3 (11%) | |
| Weight Decreased | 3 (11%) | |

Conclusions

This study shows that MS patients treated with masitinib, an oral tyrosine kinase inhibitor acting on mast cells, showed positive response in some relevant measures of their condition. Moreover, this positive action was observed in patients with PPMS and rfSPMS, subpopulations for whom there are practically no currently available treatments. This proof-of-concept data supports a confirmatory phase 2b/3 clinical trial to further evaluate the efficacy and safety of masitinib versus placebo in patients suffering from PPMS or rfSPMS. Accordingly, a tyrosine kinase or MC inhibitor such as masitinib is considered to be active in the treatment of human MS, and in particular of PPMS and rfSPMS.

EXAMPLE 2

Clinical Evaluation in Patients with RRMS or Relapsing SPMS

A phase 2a, randomized, open-label, non-controlled, proof-of-concept clinical trial, designed to evaluate the efficacy and safety of oral masitinib on active lesions in adult patients having RRMS or relapsing SPMS (rSPMS) over 36-week treatment duration.

Methods

Study Design and Treatment

A multicenter, open-label, non-controlled, proof-of-concept clinical trial, designed to evaluate the efficacy and safety of oral masitinib administered at 3 or 6 mg/kg/day for 36 weeks in patients with RRMS or rSPMS. The study was initiated in June 2005 and was discontinued prematurely after 4 patients had been included between August 2005 and February 2007, due a request by the French Health Authorities whilst questions were being answered concerning carcinogenicity risks linked to the metabolite AB2436.

Patients

Male and female patients aged 18 to 60 years, presenting with a RRMS or rSPMS with at least one relapse within the last 24 months. Eligible patients should have had at least one active gadolinium lesion at any of the three MRI performed during an 8 week run-in period and an EDSS score within the range of 2.0 to 6.5 inclusive.

Results

Baseline Characteristics

At cut-off date, four patients (2 males, 2 females) were included in the study, with a mean age of 34 (range: 26-42, SD=9). Two patients were allocated to the 3 mg/kg/day arm, and the other two patients to the 6 mg/kg/day arm. One patient was withdrawn from the study at week 32 for serious adverse event (relapse of multiple sclerosis with right hemiplegia); one patient completed the study at week 36; one patient entered the study extension and completed week 84 at cut-off date and the fourth patient is still ongoing at week 24 at cut-off date.

Efficacy Analyses

All patients had their T1 gadolinium-enhancing lesion number reduced to none at consecutive time points during the study; for two patients this was maintained for 20 weeks and 76 weeks. One patient in the extension study had no T1 gadolinium-enhancing lesions at W84. During masitinib treatment, both the number and volume of T1 lesions decreased from an average 5.35 lesions in the run-in period, to 1.5 after 12 weeks, and to 0.25 after 20 weeks of treatment. The average was 1.0 lesion during the treatment period (W0 to W36). The volume of T1 lesions decreased from an average of 777 $mm^3$ in the run-in period, to 54 $mm^3$ after 12 weeks, and to 40 $mm^3$ after 20 weeks of treatment. The average was 99 $mm^3$ during the treatment period (W0 to W36).

Both number and volume of T2 hyperintense lesions and T1 hyperintense lesions remained globally stable. One patient out of four (25%) experienced three relapses during treatment. The other three patients were relapse-free at last follow-up. There was neither improvement nor progression in EDSS, which was anticipated in a 36-week study. The patient in the study extension phase at has so far maintained their EDSS score of 2.5 to W84.

Safety Analyses

Overall, treatment by masitinib was relatively well tolerated. No death was reported. Two SAES (MS relapse) were reported in one patient. The first occurred during the run-in period, and the second at W32 and led to premature study discontinuation. Both relapses were assessed as not related to masitinib. A total of 11 AEs were reported in two patients during the treatment period, all at doses of ≥6 mg/kg/day. Two severe AEs were reported (diarrhea and MS relapse) in two patients.

Conclusions

The data show that for 3/4 patients, both number and volume of T1 lesions decreased during masitinib treatment. Three patients were relapse-free for respectively: 7, 11.5 and 25 months. Accordingly, a tyrosine kinase or MC inhibitor such as masitinib is considered to be active in the treatment of human MS, and in particular of RRMS and rSPMS.

REFERENCES

Bebo B F, Jr, Yong T, Orr E L, Linthicum D S. Hypothesis: a possible role for mast cells and their inflammatory mediators in the pathogenesis of autoimmune encephalomyelitis. J Neurosci Res 1996; 45:340-8.

Bidri M, Féger F, Varadaradjalou, S Ben Hamouda N, Guillosson J J, Arock M. Mast cells as a source and target for nitric oxide. International Immunopharmacology 2001; 1(8), 1543-1558.

Bradl M, Lassmann H. Progressive multiple sclerosis. Semin Immunopathol. 2009 Sep. 3 [Epub ahead of print]

Brenner T, Soffer D, Shalit M, Levi-Schaffer F. Mast cells in experimental allergic encephalomyelitis: characterization, distribution in the CNS and in vitro activation by myelin basic protein and neuropeptides. J Neurol Sci 1994; 122: 210-3.

Brown M A, Tanzola M B, Robbie-Ryan M. Mechanisms underlying mast cell influence on EAE disease course. Mol. Immunol. 2001; 38(16-18):1373-8

Cutter G R, Baier M L, Rudick R A, Cookfair D L, Fischer J S, Petkau J, Syndulko K, Weinshenker B G, Antel J P, Confavreux C, Ellison G W, Lublin F, Miller A E, Rao S M, Reingold S, Thompson A, Willoughby E. Development of a multiple sclerosis functional composite as a clinical trial outcome measure. Brain 1999; 122:871-82.

Dubreuil P, Letard S, Ciufolini M, Gros L, Humbert M, Castéran N, Borge L, Hajem B, Lermet A, Sippl W, Voisset E, Arock M, Auclair C, Leventhal P S, Mansfield C D, Moussy A, Hermine O (2009) Masitinib (AB1010), a potent and selective tyrosine kinase inhibitor targeting KIT. PLoSONE 4(9): e7258. doi:10.1371/journal.pone.0007258.

Encinas J M, Manganas L, Enikolopov G. Nitric Oxide and Multiple Sclerosis. Current Neurology and Neuroscience Reports 2005; 5:232-238.

Esposito P, Chandler N, Kandere K, Basu S, Jacobson S, Connolly R, Tutor D, Theoharides T C. Corticotropin-releasing hormone and brain mast cells regulate blood-brain-barrier permeability induced by acute stress. J Pharmacol Exp Ther 2002; 303:1061-6.

Fischer J S, LaRocca N G, Miller D M, Ritvo P G, Andrews H, Paty D. Recent developments in the assessment of quality of life in multiple sclerosis (MS). Mult Scler 1999a; 5:251-9.

Fischer J S, Jak A J, Kniker J E, Cutter G, Rudick R. Administration and scoring manual for the multiple sclerosis functional composite. 1999b, New York: Demos.

Gilfillan A M, Tkaczyk C. Integrated signalling pathways for mast-cell activation. Nature Review Immunology 2006; 6: 218-230.

Guideline On Clinical Investigation Of Medicinal Products For The Treatment Of Multiple Sclerosis, Doc. Ref. CPMP/EWP/561/98 Rev. 1

Kurtzke J F. Rating neurologic impairment in multiple sclerosis: an expanded disability status scale (EDSS). Neurology 1983; 33:1444-52.

Letourneau R, Rozniecki J J, dimitriadou V, Theoharides T C. Ultrastructural evidence of brain mast cell activation without degranulation in monkey experimental allergic encephalomyelitis. J Neuroimmunol 2003; 145:18-26.

Lublin F D, Reingold S C. "Defining the clinical course of multiple sclerosis: results of an international survey. National Multiple Sclerosis Society (USA) Advisory Committee on Clinical Trials of New Agents in Multiple Sclerosis". (1996) Neurology 46 (4): 907-11.

McDonald W I, Compston A, Edan G, et al. (2001). "Recommended diagnostic criteria for multiple sclerosis: guidelines from the International Panel on the diagnosis of multiple sclerosis [1]". Ann. Neurol. 50 (1): 121-7. doi: 10.1002/ana.1032. PMID 11456302.

Polman C H, Reingold S C, Edan G, et al. (2005). "Diagnostic criteria for multiple sclerosis: 2005 revisions to the "McDonald Criteria"". Ann. Neurol. 58 (6): 840-6. doi: 10.1002/ana.20703. PMID 16283615.

Rejdak K, Eikelenboom M J, Petzold A, et al.: CSF nitric oxide metabolites are associated with activity and progression of multiple sclerosis. Neurology 2004, 63:1439-1445.

Skaper S D, Facci L, Romanello S, Leon A. Mast Cell Activation Causes Delayed Neurodegeneration in Mixed Hippocampal Cultures via the Nitric Oxide Pathway. J. Neurochem 1996; 66: 1157-1166.

Theoharides T C, Cochrane D E. Critical role of mast cells in inflammatory diseases and the effect of acute stress. J Neuroimmunol 2004; 146:1-12.

Theoharides T C, Kempuraj D, Kourelis T, Manola A. Human mast cells stimulate activated T cells: implications for multiple sclerosis. Ann N Y Acad. Sci. 2008; 1144:74-82

Zappulla J P, Arock M, Mars L T, Liblau R S. Mast cells: new targets for multiple sclerosis therapy? J. Neuroimmunol. 2002; 131:5-20

The invention claimed is:

1. A method for the treatment of multiple sclerosis with active disease, evidenced by relapses, wherein said method comprises administering to at least one human patient in need thereof at least one inhibitor of kinase activity selected from the tyrosine kinases of c-Kit, LYN and FYN, wherein said kinase inhibitor is masitinib or a pharmaceutically acceptable salt thereof.

2. The method according to claim 1, wherein said at least one human patient is between 2.0 to 6.5 on the expanded disability status scale (EDSS).

3. The method according to claim 1, wherein said kinase inhibitor is dose escalated by increments of 1.5 mg/kg/day to reach a maximum of 9.0 mg/kg/day.

4. The method according to claim 1, wherein said kinase inhibitor is administered twice a day.

5. The method according to claim 1, comprising a long-term administration of an effective amount of said kinase inhibitor over more than 6 months.

6. The method according to claim 5, comprising a long-term administration of an effective amount of said kinase inhibitor over more than 12 months.

7. The method according to claim 1, wherein said kinase inhibitor is to be administered orally.

8. The method according to claim 1, wherein said kinase inhibitor is administered for the treatment of relapsing forms of multiple sclerosis.

9. The method according to claim 1, wherein said kinase inhibitor is administered for the treatment of relapsing secondary progressive multiple sclerosis.

10. The method according to claim 1, wherein said kinase inhibitor is administered for the treatment of relapsing remitting multiple sclerosis.

11. The method according to claim 1, wherein said kinase inhibitor is administered for the treatment of progressive relapsing multiple sclerosis.

12. The method according to claim 1, wherein masitinib or a pharmaceutically acceptable salt thereof is masitinib mesilate.

13. A method of treatment of multiple sclerosis with active disease, evidenced by relapses, in at least one human patient comprising administering a kinase inhibitor to the at least one human patient daily at a starting dose of 3.0 to 6.0±1.5 mg/kg/day, and wherein said at least one human patient is between 1.0 to 6.5 on the expanded disability status scale (EDSS), wherein said kinase inhibitor is masitinib or a pharmaceutically acceptable salt thereof.

14. The method according to claim 13, wherein said at least one human patient is between 2.0 to 6.5 on the expanded disability status scale (EDSS).

15. The method according to claim 13, wherein said kinase inhibitor is dose escalated by increments of 1.5 mg/kg/day to reach a maximum of 9.0 mg/kg/day.

16. The method according to claim 13, wherein said kinase inhibitor is administered twice a day.

17. The method according to claim 13, comprising a long-term administration of an effective amount of said kinase inhibitor over more than 6 months.

18. The method according to claim 17, comprising a long-term administration of an effective amount of said kinase inhibitor over more than 12 months.

19. The method according to claim 13, wherein said kinase inhibitor is to be administered orally.

20. The method according to claim 13, wherein said kinase inhibitor is administered for the treatment of relapsing forms of multiple sclerosis.

21. The method according to claim 13, wherein said kinase inhibitor is administered for the treatment of relapsing secondary progressive multiple sclerosis.

22. The method according to claim 13, wherein said kinase inhibitor is administered for the treatment of relapsing remitting multiple sclerosis.

23. The method according to claim 13, wherein said kinase inhibitor is administered for the treatment of progressive relapsing multiple sclerosis.

24. The method according to claim 13, wherein masitinib or a pharmaceutically acceptable salt thereof is masitinib mesilate.

* * * * *